US008411275B1

(12) United States Patent
Ohodnicki, Jr. et al.

(10) Patent No.: US 8,411,275 B1
(45) Date of Patent: Apr. 2, 2013

(54) NANOCOMPOSITE THIN FILMS FOR HIGH TEMPERATURE OPTICAL GAS SENSING OF HYDROGEN

(75) Inventors: Paul R. Ohodnicki, Jr., Alison Park, PA (US); Thomas D. Brown, Finleyville, PA (US)

(73) Assignee: U.S. Department of Energy, Washington, DC (US)

( * ) Notice: Subject to any disclaimer, the term of this patent is extended or adjusted under 35 U.S.C. 154(b) by 0 days.

(21) Appl. No.: 13/443,223

(22) Filed: Apr. 10, 2012

(51) Int. Cl.
*G01N 21/00* (2006.01)
*G01N 21/55* (2006.01)
(52) U.S. Cl. .................. 356/445; 356/437
(58) Field of Classification Search .......... 356/432–448, 356/246; 250/343, 548.1; 436/134, 167, 436/168; 422/88, 91, 94, 83, 68.1
See application file for complete search history.

(56) References Cited

U.S. PATENT DOCUMENTS

| | | | | |
|---|---|---|---|---|
| 4,355,997 | A * | 10/1982 | Smith et al. ................ | 436/25 |
| 5,338,515 | A * | 8/1994 | Dalla Betta et al. ........ | 422/95 |
| 5,580,793 | A * | 12/1996 | Wanner ...................... | 436/144 |
| 5,941,068 | A * | 8/1999 | Brown et al. ............... | 60/297 |
| 7,249,564 | B2 * | 7/2007 | Lissianski et al. .......... | 110/345 |
| 7,864,322 | B2 | 1/2011 | Carpenter et al. | |
| 8,308,848 | B1 * | 11/2012 | Alptekin et al. ............ | 95/136 |
| 2003/0134426 | A1 * | 7/2003 | Jiang et al. ................. | 436/121 |
| 2004/0112743 | A1 * | 6/2004 | Fukatsu et al. ............. | 204/424 |
| 2009/0207413 | A1 * | 8/2009 | Carpenter et al. .......... | 356/437 |
| 2010/0210029 | A1 * | 8/2010 | Meinhart et al. ........... | 436/168 |
| 2011/0038784 | A1 * | 2/2011 | Plata et al. ................. | 423/447.1 |
| 2011/0152070 | A1 * | 6/2011 | Fansler et al. .............. | 502/183 |

OTHER PUBLICATIONS

Giangregorio et al., "Insight into Gold Nanoparticle-Hydrogen Interaction: A Way to Tailor Nanoparticle Surface Charge and Self-Assembled Monolayer Chemisorption," J. Phys. Chem. C 115 (2011).
Bus et al., "Hydrogen Chemisorption on Al2O3-Supported Gold Catalysts," J. Phys. Chem. B 109 (2005).
Joy at al., "Plasmonic Based Kinetic Analysis of Hydrogen Reactions within Au-YSZ Nanocomposites" J. Phys. Chem. C 115 (2011).

* cited by examiner

*Primary Examiner* — Sang Nguyen
(74) *Attorney, Agent, or Firm* — James B. Potts; Mark P. Dvorscak; John T. Lucas

(57) ABSTRACT

The disclosure relates to a plasmon resonance-based method for $H_2$ sensing in a gas stream at temperatures greater than about 500° C. utilizing a hydrogen sensing material. The hydrogen sensing material is comprised of gold nanoparticles having an average nanoparticle diameter of less than about 100 nanometers dispersed in an inert matrix having a bandgap greater than or equal to 5 eV, and an oxygen ion conductivity less than approximately $10^{-7}$ S/cm at a temperature of 700° C. Exemplary inert matrix materials include $SiO_2$, $Al_2O_3$, and $Si_3N_4$ as well as modifications to modify the effective refractive indices through combinations and/or doping of such materials. At high temperatures, blue shift of the plasmon resonance optical absorption peak indicates the presence of $H_2$. The method disclosed offers significant advantage over active and reducible matrix materials typically utilized, such as yttria-stabilized zirconia (YSZ) or $TiO_2$.

20 Claims, 7 Drawing Sheets

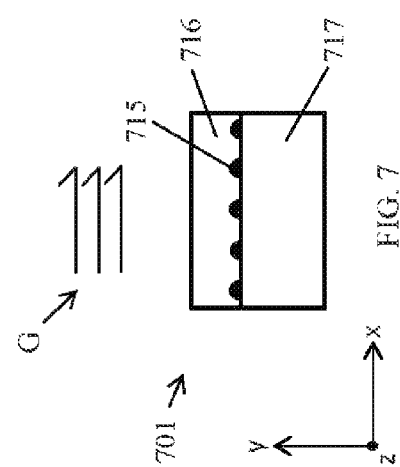
FIG. 5
FIG. 6
FIG. 7

NANOCOMPOSITE THIN FILMS FOR HIGH TEMPERATURE OPTICAL GAS SENSING OF HYDROGEN

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments relates to a method for $H_2$ sensing in a gas at temperatures greater than approximately 500° C. utilizing the shift in plasmon resonance peak position generated by a hydrogen sensing material. The hydrogen sensing material is comprised of a nanocomposite film comprised of a plurality of gold nanoparticles dispersed within, below, or above an optically transparent, wide bandgap matrix considered to be inert under the conditions in which hydrogen sensing is performed. In some cases, this matrix is specifically selected such that the nanocomposite film exhibits an effective refractive index that is less than that of the core material of an optical waveguide to enable effective waveguiding when employed as a gas sensitive cladding layer for evanescent wave absorption spectroscopy based sensing.

BACKGROUND

The enhancement of EM fields in the vicinity of metallic nanoparticles and metallic nanostructures can be explained by the phenomenon of localized surface plasmon resonance. The shape and magnitude of associated features measured in the transmission or reflection spectra from these metallic structures depend on the enhanced scattering and absorption of light at specific wavelengths. The details of the extinction cross-section enhancement over a finite wavelength range is affected by several different factors that include the characteristic optical constants and geometry of the nanostructures illuminated by incident light as well as the optical constant of the surrounding matrix phase.

The origin of plasmon resonances are collective oscillations of the conduction band electrons and they result from the presence of interfaces for nanoparticles and films of a select group of materials which include the noble metals Ag, Cu, and Au. Localized surface plasmons are excited when light is incident on metallic nanoparticles which typically have dimensions smaller than the wavelength of the incident light. At certain characteristic wavelengths, one or more resonant modes are excited in the nanoparticles leading to a significant enhancement in absorbed and scattered light and a strong increase in the electromagnetic fields in the vicinity of the particles. Localized surface plasmons can be detected as resonance peaks in the absorption and scattering spectra of the metallic nanoparticles. Nanostructures made up of noble metals, such as gold, silver, and copper, are well known to exhibit localized surface plasmon resonance (LSPR) phenomena.

The collective oscillation of the free electrons are also sensitive to changes in the size of the particle. For example, gold nanoparticles embedded in a transparent matrix phase with a real dielectric constant similar to that of $SiO_2$ ($\in$~2.25) and average diameters in the range of approximately 5-10 nm, strongly absorb at visible wavelengths with a maximum absorbance near 520 nm. In this particular case, the energy required to excite the surface plasmon lies in the visible region of the spectrum. With increases in the Au particle size, a shift in the peak of the optical absorption to longer wavelengths is observed due to the excitation of higher-order resonant modes. The relative magnitude of the scattering cross-section also increases as compared to the absorption cross-section resulting in particles that strongly scatter light rather than absorb it for particle sizes approaching 100 nm. In addition to being size-dependent, the plasmon resonance band is sensitive to changes in the dielectric properties of the surrounding medium. For transparent matrix media with large dielectric constants the energy required to collectively excite the electrons is decreased thereby shifting the peak in the extinction cross-section to lower energies and longer wavelengths.

The strong dependence of the optical extinction peak on a number of material dependent parameters provides the nanoparticles with an inherent sensing ability. For visible light, generally only changes in refractive index occurring at distances within about 200 nm of the particle surface result in changes to the optical properties of the nanoparticles. The plasmon resonance behavior of nanoparticles are particularly sensitive to adsorption directly on the particle surface and hence biological sensing based on analyte absorption by nanoparticles and subsequent modifications of the absorbance maximum is currently an area of significant effort.

The changes in the absorbance maxima generated by the localized surface plasmon resonance effect has also been utilized extensively for gas sensing applications in the low and intermediate temperature ranges. A select few researchers in the field have also applied Au incorporated films to optical gas sensing at higher temperatures. However, current technical literature suggests that the fundamental response of technically useful Au/metal oxide composite films for high temperature (>500° C.) optical gas sensing applications requires the selection of a matrix phase that plays an active role in the gas sensing process. Two potential ways that such an active role can be played include (1) a change in the free carrier density of the matrix phase followed by an electronic charge transfer from the matrix to the nanoparticle and (2) a change in the effective dielectric constant of the matrix phase. Both of these effects would result in a modification to the extinction peak of Au nanoparticles associated with the localized surface plasmon resonance effect that could be detected through optical based monitoring techniques. As a result, nanoparticles are generally embedded in reducible and oxygen conducting matrices such as $TiO_2$ or yttria-stabilized zirconium (YSZ) for high temperature optical sensing. Current technical literature suggests that technologically useful optical responses associated with plasmon absorption peak shifts require the presence of oxygen in the sensing environment and reduction of the matrix phase with associated changes in the oxygen vacancy concentration. See e.g., Sirinakis et al., "Development and Characterization of Au-YSZ Surface Plasmon Resonance Based Sensing Materials: High Temperature Detection of CO," *J. Phys. Chem. B* 110 (2006); and see Ando et al., "Optical CO sensitivity of Au—CuO composite film by use of the plasmon absorption change," *Sensors and Actuators B* 96 (2003); and see U.S. Pat. No. 7,864,322 B2 to Carpenter et al. This approach has the disadvantage of requiring the concurrent presence of $O_2$ as a gaseous constituent in order to affect charge transfer and additionally produces a sensor which responds in a similar manner to a variety of reducing gases outside of $H_2$. Further, the response mechanism of the gas sensor requires a non-negligible partial pressure of $O_2$ within the gas stream to be sensed. In the absence of $O_2$ as a gaseous constituent, slow kinetics and a saturated sensing response at $H_2$ concentrations as low as 0.1% were reported and the mechanism may still rely on an interaction between the matrix material and the sensed environment. See e.g. Joy et al., "Plasmonic Based Kinetic Analysis of Hydrogen Reactions within Au-YSZ Nanocomposites," *J. Phys. Chem. C* 115 (2011).

It would be advantageous to provide a plasmon-based methodology for high temperature $H_2$ sensing based on a hydrogen sensing material that is not contingent upon a direct interaction between the matrix oxide and the ambient gas atmosphere causing a change in effective dielectric constant and/or concentration of oxygen vacancies with a measurable effect on the localized surface plasmon resonance (LSPR) extinction cross-section. The former impacts the LSPR behavior directly while the latter affects it through changes in the density of electrons (n-type oxides) or holes (p-type oxides) in the matrix phase followed by charge transfer between the nanoparticle and the matrix. It would also be advantageous to provide a methodology that does not require the presence of $O_2$ within the sensing environment.

Preferably, such a methodology would be based on a direct interaction between the nanoparticle and the sensed $H_2$, particularly at temperature in excess of approximately 500° C. Currently, plasmonic responses to such direct interactions have been limited to a gold nanoparticle/silicon substrate material exposed to atomic H at room temperature. See Giangregorio et al., "Insight into Gold Nanoparticle-Hydrogen Interaction: A Way To Tailor Nanoparticle Surface Charge and Self-Assembled Monolayer Chemisorption," J. Phys. Chem. C 115 (2011). Further, investigations on the adsorption of diatomic $H_2$ on gold nanoparticles has been limited to temperatures of around 250° C., significantly below the 500° C. or greater temperatures desired for certain operations including, but not limited to, power generation technologies utilizing fossil fuels including coal gasification, solid oxide fuel cells, gas turbines, and advanced combustion systems. See e.g., Bus et al., "Hydrogen Chemisorption on $Al_2O_3$—Supported Gold Catalysts," *J. Phys. Chem. B* 109 (2005). It would be advantageous if a methodology were provided whereby nanoparticles dispersed on, beneath, or embedded within a matrix could be utilized for a plasmon-based detection of $H_2$ generated through a direct interaction between the nanoparticles and the sensed $H_2$, and additionally advantageous if the methodology were effective in gas streams at temperatures in excess of approximately 500° C. such that they were relevant for a number of fossil fuel based energy production applications.

Disclosed here is a method for $H_2$ sensing in a gas at temperatures greater than approximately 500° C. which utilizes shifts in a plasmon resonance peak position generated by a hydrogen sensing material. The hydrogen sensing material is comprised of a plurality of gold nanoparticles dispersed in a wide bandgap matrix with a low oxygen ion conductivity that is considered to be inert at the temperatures and gas atmospheres of interest. The method disclosed offers significant advantage over materials typically utilized for plasmon-based high temperature sensing such as yttria-stabilized zirconia (YSZ) or $TiO_2$, including enhanced thermal stability, improved selectivity to $H_2$ with respect to other reducing gases, and increased stability of nanoparticle diameter, among other advantages. In addition, several candidates for inert matrix materials (e.g. $SiO_2$, $Al_2O_3$, $MgF_2$ doped $SiO_2$, mixed $SiO_2/Al_2O_3$) exhibit relatively low values of refractive indices for fully densified films ranging from less than ~1.5 to greater than ~1.7. In contrast, such low values of effective refractive index cannot be obtained in fully dense films of reducible or high oxygen conducting oxides such as $TiO_2$ and YSZ. This property is advantageous as it enables integration of nanocomposite films directly with optical fiber based sensors as a gas sensitive cladding layer in an evanescent wave absorption spectroscopy based sensing configuration while maintaining the conditions necessary for waveguiding in the low refractive index core material. Typical core materials for such applications include $SiO_2$ (refractive index ~1.5) for silica-based optical fibers and $Al_2O_3$ (refractive index ~1.7) for sapphire based optical fibers.

These and other objects, aspects, and advantages of the present disclosure will become better understood with reference to the accompanying description and claims.

SUMMARY

The disclosure provides a method for $H_2$ sensing in a gas at temperatures greater than about 500° C. by utilizing the shifts in plasmon resonance peak position generated by a hydrogen sensing material, where the hydrogen sensing material is comprised of a plurality of gold nanoparticles dispersed in an inert matrix. The hydrogen sensing material is in contact with a monitored stream comprised of gaseous constituents and periodically comprised of diatomic hydrogen $H_2$, having a concentration which may vary over time. At the high temperatures of the monitored stream, the hydrogen sensing material exhibits a plasmon resonance optical absorption peak which undergoes a blue shift to lower wavelengths in response to the presence of $H_2$.

The hydrogen sensing material is comprised of gold nanoparticles having an average nanoparticle diameter of less than about 100 nanometers. The gold nanoparticles are dispersed in an inert matrix having a bandgap greater than or equal to 5 electron volts (eV), and an oxygen ion conductivity of less than approximately $10^{-7}$ S/cm at a temperature of 700° C. Exemplary inert matrix materials include $SiO_2$, $Al_2O_3$, and $Si_3N_4$ as well as derivatives such as $MgF_2$ doped $SiO_2$, and mixtures of $SiO_2/Al_2O_3$. In certain embodiments, matrix materials are specifically chosen to optimize the effective refractive index of the hydrogen sensing material for use as gas sensitive cladding layers in optical waveguide based sensors. Negligible changes in refractive index and a limited number of free carriers of the inert matrix are expected in response to any reducing species that may occur in a monitored stream such that modifications to the LSPR features of Au nanoparticles are dominated by direct interactions between the Au particle and the ambient atmosphere. Rather than playing an active role in the gas sensing mechanism, the primary role of the inert matrix is two-fold: (1) to mitigate the coarsening of gold nanoparticles under the rigorous high temperature conditions of this disclosure and (2) to tailor the effective refractive index of the nanocomposite thin film for optimized sensing response when integrated with an optical waveguide based sensing platform. In some cases, the matrix phase may also be selected to improve hydrogen selectivity by inhibiting chemical diffusion of species other than hydrogen thereby preventing them from reaching the surface of embedded Au nanoparticles.

The hydrogen sensing material utilized in the method of this disclosure may be prepared using means known in the art for the production of gold nanoparticles dispersed within a supporting matrix including sol-gel based wet chemistry techniques, impregnation techniques, implantation techniques, sputtering techniques, and others. The sensing material may be deposited as a single monolithic layer or through multi-layered deposition involving a single technique or a combination of several film deposition techniques. The hydrogen sensing material and the associated method disclosed offers significant advantages over materials typically utilized for plasmon-based high temperature sensing such as yttria-stabilized zirconia (YSZ) or $TiO_2$, including enhanced thermal stability, relative insensitivity to reducing gases beyond $H_2$, and increased stability of nanoparticle diameter, among others.

The novel process and principles of operation are further discussed in the following description.

BRIEF DESCRIPTION OF THE DRAWINGS

FIG. 5 illustrates an embodiment of the hydrogen sensing material.

FIG. 6 illustrates an additional embodiment of the hydrogen sensing material.

FIG. 7 illustrates an additional embodiment of the hydrogen sensing material.

DETAILED DESCRIPTION

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method for $H_2$ sensing at temperatures greater than about 500° C. based on the resulting shifts in plasmon resonance peak position generated by a hydrogen sensing material comprised of gold nanoparticles dispersed in an inert matrix.

The disclosure provides a method for $H_2$ sensing in a gas at temperatures greater than about 500° C. by utilizing the shifts in plasmon resonance peak position generated by a particular hydrogen sensing material. The hydrogen sensing material is comprised of a plurality of gold nanoparticles dispersed in an inert matrix. The gold nanoparticles have an average nanoparticle diameter of less than about 100 nm, and the inert matrix has a bandgap exceeding 5 eV and an oxygen ion conductivity of less than approximately $10^{-7}$ S/cm at a temperature of 700° C. The method disclosed offers significant advantages over alternative high temperature plasmon-based gas sensing materials incorporating active matrix materials such as yttria-stabilized zirconia (YSZ) or $TiO_2$, including enhanced thermal stability, relative insensitivity to reducing gases beyond $H_2$, the ability to tune effective refractive indices in the range required to be compatible with optical waveguide based sensors, and others.

Figure 1:
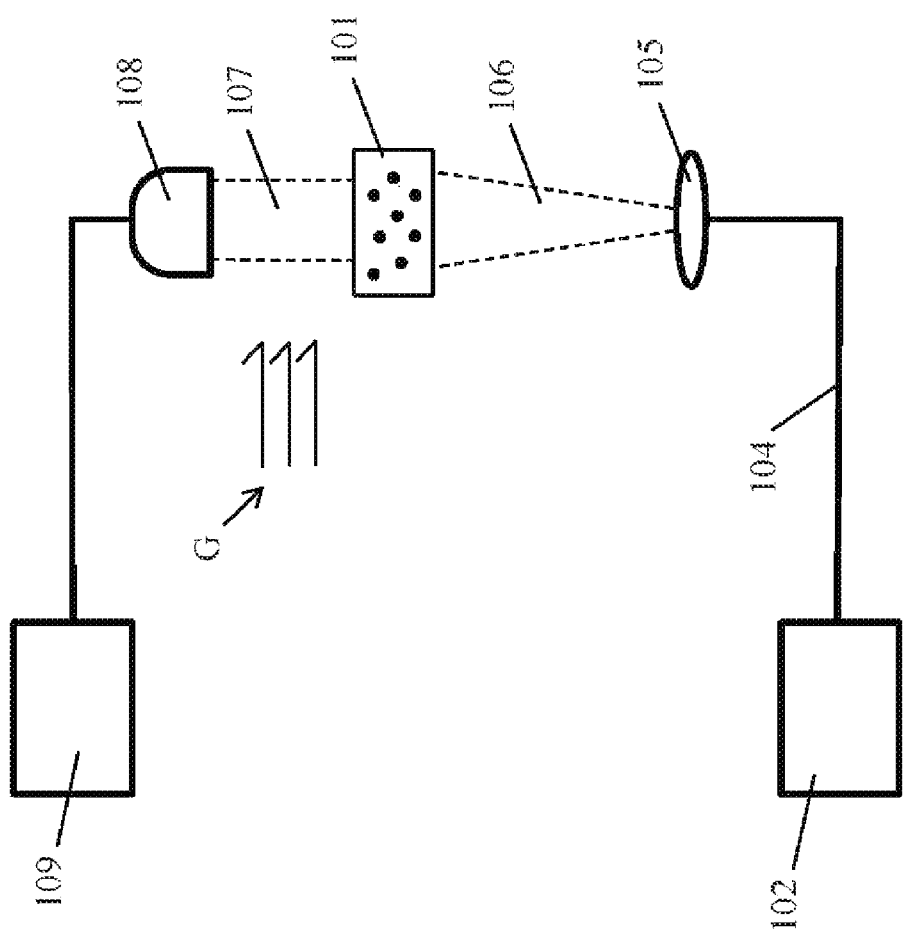
FIG. 1 illustrates a methodology for sensing $H_2$ in a high temperature gas stream using the hydrogen sensing material.

The basic principles of the method are illustrated at FIG. 1. At FIG. 1, light from light source 102 is directed along an optical fiber 104 and focused by lens 105 producing incident light 106 illuminating hydrogen sensing material 101. Generally, incident light 106 is comprised of light having wavelengths in the visible spectrum. Concurrently, exiting light 107 is collected behind the specimen using a probe 108 of spectrophotometer 109. Data generated by spectrophotometer 109 or supporting equipment is processed and the extinction spectrum is displayed. See e.g., Sarid, Dror and Challener, William, *Modern Introduction to Surface Plasmons: Theory, Mathematica Modeling, and Applications*, Cambridge University Press, 2010, among many others. The extinction spectrum indicates the selective photon absorption or scattering of light at certain wavelengths by hydrogen sensing material 101.

Hydrogen sensing material 101 is additionally in contact with a monitored stream G. Monitored stream G is comprised of gaseous constituents and has a temperature greater than about 500° C. The gaseous constituents within monitored stream G are periodically comprised of diatomic hydrogen $H_2$, the concentration of which may vary over time. Additionally, and as will be discussed, hydrogen sensing material 101 is comprised of gold nanoparticles dispersed in an inert matrix. It has been found that, at the high temperature of monitored stream G, hydrogen sensing material 101 exhibits a plasmon resonance optical absorption peak at a plasmon resonance peak position which undergoes a blue shift to lower wavelengths in response to the presence of $H_2$.

Figure 2:
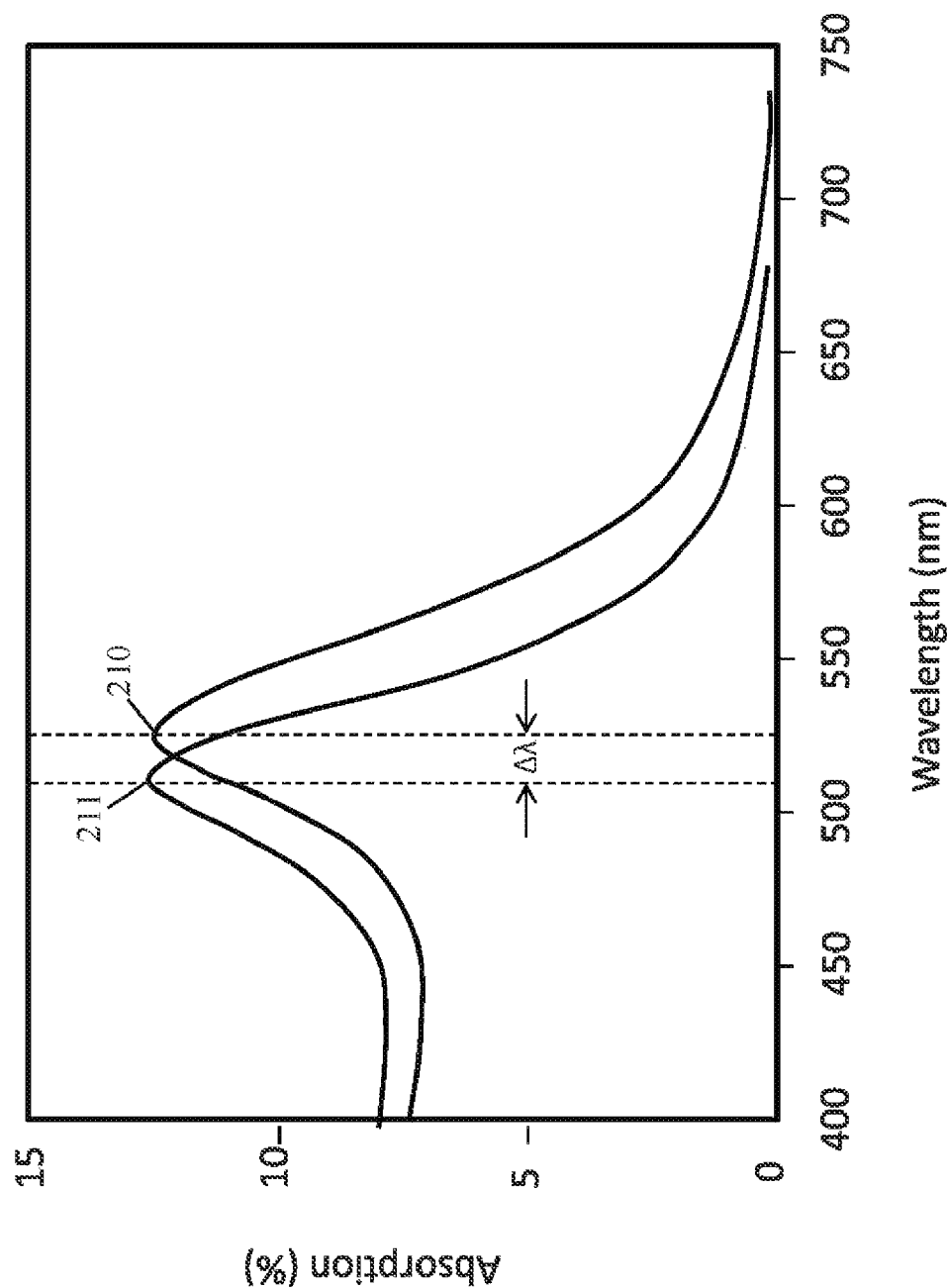
FIG. 2 illustrates the peak shift of a plasmon resonance optical absorption peak in response to $H_2$.

As an example, FIG. 2 illustrates a plasmon resonance optical absorption peak 210 generated when monitored stream G is comprised of air. In the substantial absence of $H_2$, plasmon resonance optical absorption peak 210 occurs at a plasmon resonance peak position of generally around 525 nm. In contrast, when monitored stream G is comprised of about 4% $H_2$, remainder $N_2$, the absorption peak blue shifts to plasmon resonance optical absorption peak 211, with a plasmon resonance peak position occurring at a wavelength of generally around 510 nm. Correspondingly, the presence of $H_2$ within monitored stream G and at the high temperatures of monitored stream G may be detected based on the peak shift $\Delta\lambda$ for the plasmon resonance peak positions of plasmon resonance optical absorption peaks 210 and 211.

The peak shift $\Delta\lambda$ may be determined directly in a manner similar to that indicated at FIG. 2, where plasmon resonance peak positions are determined and compared to indicate the presence of $H_2$ in monitored stream G. Alternatively, alterations to the plasmon resonance peak positions and the resulting peak shift $\Delta\lambda$ may be inferred by detecting a change in absorption characteristics at any monitored wavelength, provided the change in absorption characteristics is consistent with a blue shift to lower wavelengths of the plasmon resonance peak positions.

Within this disclosure, "plasmon resonance optical absorption peak" means the maximum value of absorption which occurs when a spectrum of incident light is compared to a spectrum of exiting light, where the incident light is comprised of light illuminating the hydrogen sensing material, and where the exiting light is comprised of some portion of the incident light transmitted by the hydrogen sensing material. A "plasmon resonance peak position" means the wavelength at which the plasmon resonance optical absorption peak occurs. As is understood, absorption spectroscopy based on a comparison of the incident light and the exiting light indicates the light absorption as a function of wavelength that occurs as a result of interaction between the incident light and the hydrogen sensing material, and may serve to identify the plasmon resonance optical absorption peak of this disclosure. See e.g., Ingle, James D., and Stanley R. Crouch, *Spectrochemical analysis*, Englewood Cliffs, N.J.: Prentice Hall, 1988, among others. Similarly, a "peak shift" means a wavelength shift between a first and second plasmon resonance peak position. For example, peak shift $\Delta\lambda$ at FIG. 2.

Figure 3:
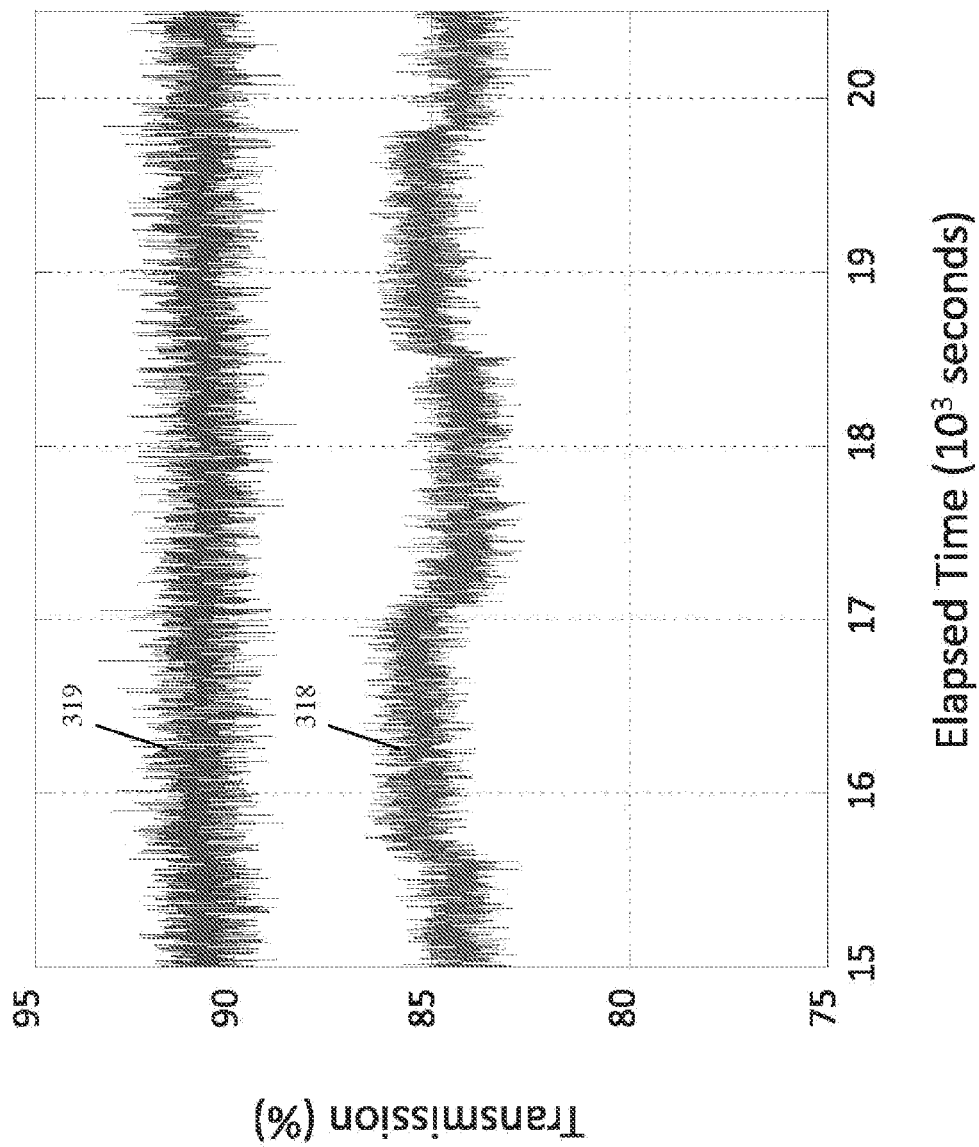
FIG. 3 illustrates the change in transmission characteristics in response to $H_2$ at high temperature at a specific wavelength.
Figure 4:
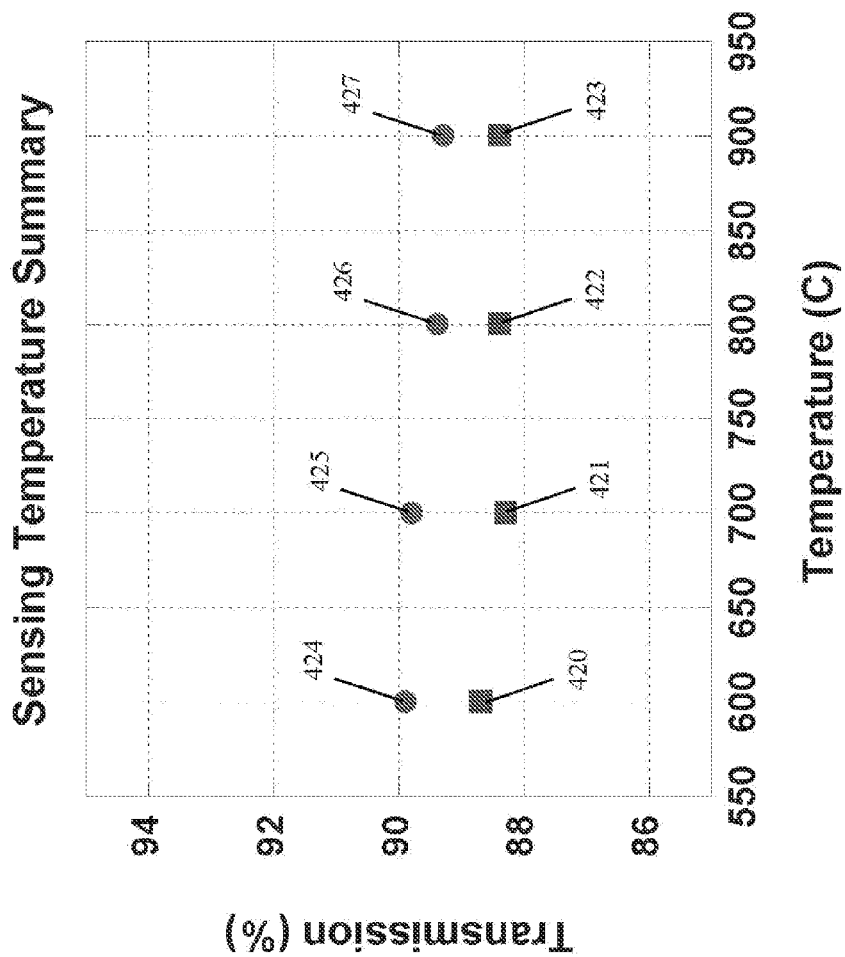
FIG. 4 illustrates the change in transmission characteristics in response to $H_2$ at a specific wavelength for a variety of temperatures.

As a further example, FIG. 3 demonstrates a response of the hydrogen sensing material in an 800° C. atmosphere alternating between an air and a 4% $H_2$, remainder $N_2$ environment. Trace 318 illustrates a change in transmission based on spectroscopy analysis of exiting light at a wavelength of 550 nm, while trace 319 illustrates a median change in transmission based on spectroscopy analysis of exiting light at a wavelength of 800 nm. As is understood, the changes in transmission are caused by changes in absorption at the specific wavelength. At FIG. 3, the hydrogen sensing material is exposed to the air environment generally between 15 and 15.5 $10^3$ seconds, 17 and 18.6 $10^3$ seconds, and after 19.7 $10^3$ seconds. Similarly, the hydrogen sensing material is exposed to the alternating 4% $H_2$, remainder $N_2$ environment generally between 15.5 and 17 $10^3$ seconds and between 18.6 and 19.7 $10^3$ seconds. As illustrated, exposure to the 4% $H_2$, remainder $N_2$ significantly increases the transmission characteristics and indicates a concurrent decrease in the absorption characteristics at the 550 nm wavelength monitored, reflecting the blue shift to lowed wavelengths indicated at FIG. 1. Wavelength specific changes in absorption such as those indicated at FIG. 3 may be utilized to indicate a peak shift such as peak shift $\Delta\lambda$ at FIG. 2, and may serve as a useful indication of $H_2$ presence at the high temperatures of this disclosure. Additionally, as indicated at FIG. 4, the response is relatively temperature insensitive. FIG. 4 illustrates the change in transmission of the hydrogen sensing material at a wavelength of 600 nm over a range of temperatures as the atmosphere is alternated between air and the 4% $H_2$, remainder $N_2$ environment. Points 420, 421, 422, and 423 indicate measured transmission characteristics in the air environment at the temperatures indicated, while points 424, 425, 426, and 427 indicate corresponding transmission characteristics in the 4% $H_2$, remainder $N_2$ environment. As illustrated, the response of the hydrogen sensing material is relatively constant over a changing temperature, and reflects the blue shift indicated at FIG. 1. This consistency with temperature tends to obviate any concurrent necessity for temperature measurement in order to utilize the hydrogen sensing material for the detection of hydrogen.

Hydrogen sensing material 101 is comprised of a plurality of gold nanoparticles dispersed in an inert matrix, where the gold nanoparticles are individually comprised of elemental gold. Preferably, an individual gold nanoparticle is comprised of at least 50 weight percent (wt %) elemental gold, and more preferably, at least 90 wt % elemental gold. Additionally, the plurality of gold nanoparticles has an average nanoparticle diameter of less than about 100 nanometers. The average nanoparticle diameter may be determined using various methods known in the art for the sizing of nanoparticles, for example, scanning electron microscopy (SEM), atomic force microscopy (AFM), and transmission electron microscopy (TEM) methods. Preferably, the average particle size is determined through image analysis by capturing a sample of typically at least 100 nanoparticles, more preferably at least 300 nanoparticles. However, the method by which an average nanoparticle diameter is determined is not limiting within this method. Within this method, it is only necessary that gold nanoparticles are individually comprised of elemental gold, and that the plurality of gold nanoparticles has an average nanoparticle diameter of less than about 100 nanometers. In an embodiment, the average nanoparticle diameter is less than about 50 nanometers. In a further embodiment, the average nanoparticle diameter is less than about 10 nanometers.

It is understood that the nanoparticles of this disclosure are not limited to strictly spherical shapes, and that the plurality of gold nanoparticles may be comprised of shapes such as triangular prisms, disks, shells, wires, rods, and others. When such structures are present, the average particle diameter refers and is equivalent to an equivalent circular diameter (ECD), which connotes the diameter of a circle with area equal to that of the projection of the particle on a plane. See e.g., Xu et al, "Comparison of sizing small particles using different technologies," *Powder Technology* 132 (2003).

Within hydrogen sensing material 101, the gold nanoparticles are dispersed in the inert matrix. As used herein, "dispersed" means that individual gold nanoparticles comprising the plurality of gold nanoparticles in hydrogen sensing material 101 are sufficiently separated such that hydrogen sensing material 101 displays an electrical conductance at least an order of magnitude less than the electrical conductance of bulk gold under an equivalent temperature condition, such that the electrical conductance is less than $\frac{1}{10}^{th}$ of the electrical conductance of the bulk gold. Such a condition can be determined using various methods for the evaluation of proximity to a percolation limit in supported nanoparticle systems. See e.g. Trudeau et al., "Competitive transport and percolation in disordered arrays of molecularly linked Au nanoparticles," *J. Chem. Phys.*, Vol. 117 (2002), among others. Additionally, in an embodiment, an average spacing between individual gold nanoparticles is at least five times greater than the average nanoparticle diameter, where average spacing indicates the average displacement between a gold nanoparticle and a nearest gold nanoparticle neighbor. For a given gold nanoparticle, the nearest gold nanoparticle neighbor may be determined through a variety of statistical methods known in the art, such as fixed radius analysis, minimal spanning trees, Voronoi polygons, k-nearest neighbor algorithms, and other established nearest neighbor methodologies. See e.g., Dussert et al., "Minimal spanning tree: A new approach for studying order and disorder," *Phys. Rev. B*, 34 (5) (1986), and see Aurenhammer, "Voronoi Diagrams—A Survey of a Fundamental Geometric Data Structure," *ACM Comput. Surv.*, 23(3) (1991), and see Cover et al., "Nearest Neighbor Pattern Classification," *IEEE T. Inform. Theory* 13(1) (1967), among others. The displacement between the given gold nanoparticle and the nearest gold nanoparticle neighbor may be determined using techniques such as scanning electron microscopy, atomic force microscopy, and transmission electron microscopy, and the average spacing may be determined as the average value over some statistically significant population of gold nanoparticles, for example at least 100 gold nanoparticles.

The gold nanoparticles may be dispersed relatively uniformly or non-uniformly with respect to the inert matrix, provided that the nanoparticles are dispersed within the meaning of the definition discussed above. For example, FIG. 5 illustrates hydrogen sensing material 501 in contact with monitored stream G, where hydrogen sensing material 501 is comprised of a plurality of gold nanoparticles such as gold nanoparticle 515 and an inert matrix 516, and where hydrogen sensing material 501 is further in contact with a substrate 517. At FIG. 5, the plurality of gold nanoparticles are concentrated in a region of inert matrix 516 in spatial proximity to the bulk of monitored stream G, such that the relative concentration of gold nanoparticles decreases or disappears within inert matrix 516 as displacement occurs in a negative direction of the y-axis illustrated. Similarly, FIG. 6 illustrates hydrogen sensing material 601 in contact with monitored stream G, where hydrogen sensing material 601 is comprised of a plurality of gold nanoparticles such as gold nanoparticle 615 and inert matrix 616, and where hydrogen sensing material 601 is further in contact with a substrate 617. In contrast to FIG. 5, at FIG. 6 the plurality of gold nanoparticles are distributed relatively homogenously through inert matrix 616, such that the relative concentration of gold nanoparticles is substantially similar within inert matrix 616 as displacement occurs in a negative direction of the y-axis illustrated. Finally, FIG. 7 illustrates hydrogen sensing material 701 in contact with monitored stream G, where hydrogen sensing material 701 is comprised of a plurality of gold nanoparticles such as gold nanoparticle 715 and inert matrix 716, and where hydrogen sensing material 701 is further in contact with a substrate 717, and depicts the plurality of gold nanoparticles concentrated in a region of inert matrix 716 such that the relative concentration of gold nanoparticles increases within inert matrix 716 as displacement occurs in a negative direction of the y-axis illustrated, and decreases or disappears as displacement occurs in a positive direction of the y-axis illustrated. However, arrangements such as those in FIGS. 5, 6, and 7 are exemplary only, and the relative concentrations of gold nanoparticles in varying regions of the inert matrix are not limiting within this disclosure. Within this disclosure, it is only necessary that the gold nanoparticles are sufficiently separated such that the hydrogen sensing material displays an electrical conductance at least an order of magnitude less than the electrical conductance of bulk gold under an equivalent temperature condition, as discussed above.

The inert matrix supporting the plurality of gold nanoparticles is permeable at least to some degree to the incident light at wavelengths corresponding to the plasmon resonance peak positions. For example, when plasmon resonance peak positions are expected to occur within a light wavelength range from about 500 nm to about 600 nm, the inert matrix is permeable at least to some degree to the incident light at wavelengths from about 500 nm to about 600 nm. In an embodiment, the inert matrix is permeable at least to some degree to light at wavelengths over the visible spectrum. Here "visible spectrum" connotes light having wavelengths from about 400 nm to about 750 nm. The optical properties of the inert matrix are such that the inert matrix has a refractive index greater than one.

Additionally, the inert matrix has a bandgap greater than or equal to 5 eV, and has an oxygen ion conductivity less than approximately $10^{-7}$ S/cm at a temperature of 700° C., where the oxygen ion conductivity is either known from compiled sources or determined using techniques known in the art, such as the oxygen permeation method. See e.g. Kagomiya et al., "Oxygen permeation and microstructure of intergrowth perovskite Sr—La—Fe—Co based mixed conductive ceramics," *J. Ceram. Soc. Jpn.* 117 (9) (2009); and see Chen et al., "Ionic conductivity of perovskite $LaCoO_3$ measured by oxygen permeation technique," *J. Appl. Electrochem.* 27 (1997), among others. The inert matrix is generally based upon a stoichiometric dielectric material, such as $SiO_2$, $Si_3N_4$, or $Al_2O_3$. In some cases, the inert matrix may consist of more complex systems such as $MgF_2$-doped $SiO_2$, or mixed $SiO_2$/$Al_2O_3$ to tailor the effective refractive indices for optimized sensing response in optical waveguide based sensing applications. Such an inert matrix as defined within this disclosure has limited free carriers, and can be expected to display negligible change in refractive index in response to reducing species that may occur in a monitored stream even at the high temperature conditions of interest relevant for this disclosure. Additionally, the inert matrix acts to mitigate the coarsening of gold nanoparticles which would otherwise occur under the high temperature conditions of this disclosure. The temperatures conditions of this disclosure are well above the Tammann temperature for Gold (395° C.) where metal mobility becomes significant. Coarsening of the gold nanoparticles is significantly reduced when dispersed in the inert matrix of this disclosure, as opposed to other common matrix materials such as $TiO_2$. See e.g., Veith et al., "Thermal stability and catalytic activity of gold nanoparticles supported on silica," *J. Catal.* 262 (2009).

Figure 8:
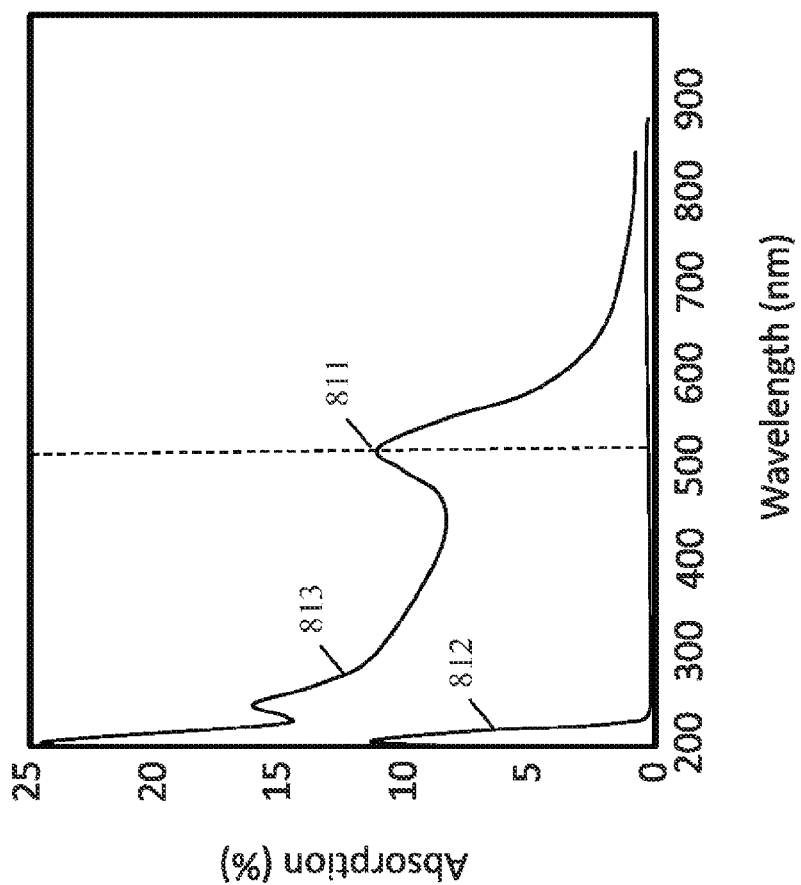
FIG. 8 illustrates a plasmon resonance optical absorption peak for a particular embodiment of the hydrogen sensing material.

FIG. 8. illustrates the plasmon resonance response of a particular embodiment of the hydrogen sensing material and indicates that the plasmon resonance optical absorption peak observed is dependent on the presence of gold nanoparticles. The particular embodiment illustrated at FIG. 8 is comprised of gold nanoparticles having an average nanoparticle diameter less than about 10 nm, dispersed in an $SiO_2$ inert matrix. The quantity Absorption (%) indicates the total amount of incident light on the film absorbed for a given wavelength as indicated based on comparison by absorption spectroscopy between incident light and exiting light following transmission through both the Au/$SiO_2$ material and an $SiO_2$ material without gold nanoparticles present. Response 812 illustrates the absorption of the $SiO_2$ material without dispersed Au nanoparticles, while response 813 illustrates the absorption of the Au/$SiO_2$ material. In contrast to response 812, response 813 indicates a plasmon resonance optical absorption peak 811 with a plasmon resonance peak position generally around 525 nm, demonstrating the impact of the gold nanoparticles. The hydrogen sensing material of this disclosure above is utilized to detect the presence of $H_2$ in a monitored stream having a temperature of at least approximately 500° C. based on a blue shift of plasmon resonance peak 811 to lower wavelengths in the presence of diatomic $H_2$. For example, the peak shift $\Delta\lambda$ of FIG. 2, which results when an Au/$SiO_2$ hydrogen sensing material is exposed to an atmosphere of 4% $H_2$, remainder $N_2$, at a temperature of approximately 800° C.

The detection of $H_2$ using gold nanoparticles dispersed in an inert matrix as described above is a surprising capability. Typically, in gas sensing operations utilizing gold nanoparticles, the gold nanoparticles are embedded in a matrix such as $TiO_2$ or YSZ. In these materials, the bulk defect chemical equilibria are strongly affected by ambient gas conditions, and the materials are oxygen conductors at the temperatures of interest. The sensing mechanism is therefore attributed to the presence of oxygen in the sensing environment and reduction of the matrix, leading to interfacial charge-transfer at the perimeter of the Au nanoparticles which alters the position and shape of the SPR band. See e.g., Sirinakis et al., "Development and Characterization of Au-YSZ Surface Plasmon Resonance Based Sensing Materials: High Temperature Detection of CO," *J. Phys. Chem. B* 110 (2006); and see Ando et al., "Optical CO sensitivity of Au—CuO composite film by use of the plasmon absorption change," *Sensors and Actuators B* 96 (2003); and see U.S. Pat. No. 7,864,322 B2 to Carpenter et al. Similarly, in other approaches which utilize gold nanoparticles for $H_2$ detection, atomic H+ may act as a donor to the matrix material, leading to plasmon resonance shifts. See e.g. Joy et al., "Plasmonic Based Kinetic Analysis of Hydrogen Reactions within Au-YSZ Nanocomposites," *J. Phys. Chem. C* 115 (2011). The inert matrix as defined in this disclosure mitigates those modes of operation.

Additionally, the detection of $H_2$ using gold nanoparticles at the elevated temperatures of this disclosure is a surprising capability. Hydrogen uptake by the gold nanoparticles may be responsible for plasmonic sensing with the inert matrix of this disclosure under certain testing conditions, and activated hydrogen chemisorption occurs as an activated process at temperatures up to at least 250° C. See e.g., Bus et al. However, hydrogen uptake measurements at this lower temperature do not directly extrapolate to the extended temperatures of this disclosure, due to the unknown variance and impact of kinetic and thermodynamic factors on hydrogen adsorption as temperature increases. A useful optical response associated with direct hydrogen chemisorption on Au nanoparticle surfaces at temperatures as high as 900° C. would not be expected or predictable based on the low temperature indications of hydrogen uptake.

The hydrogen sensing material utilized in the method of this disclosure may be prepared using means known in the art for the production of gold nanoparticles dispersed in a supporting matrix, including sol-gel wet chemistry based techniques, impregnation techniques, implantation techniques, sputtering techniques, and others. See e.g., De, "Sol-Gel Synthesis of Metal Nanoclusters—Silica Composite Films," *J. Sol-Gel Sci. Techn.* 11 (1998); and see Delannoy et al., "Preparation of supported gold nanoparticles by a modified incipient wetness impregnation method," *J. Phys. Chem. B* 110(45) (2006); and see Veith et al., "Magnetron sputtering of gold nanoparticles onto WO3 and activated carbon," *Catal. Today* 122 (2007); and see Garcia-Serrano et al., "Synthesis and characterization of Au nanoparticles in Al2O3 matrix," *Int. J. Hydrogen Energ.* 28 (2003), among many others. Generally, rigorous calcination schedules will improve the temperature stability of the resulting material under the reducing conditions of this disclosure. A high calcination temperature and long calcination time may ensure that the resulting hydrogen sensing material is properly aged, so that any optical property changes occurring in the material during sensing operations at the higher temperatures of this disclosure can be attributed to $H_2$ concentration of the monitored stream. In an embodiment, treatment temperature is ramped and held at a maximum calcination temperature of at least 800° C. In an additional embodiment, treatment temperature is ramped from about 20° C. to about 950° C. over about 10 hours, held at about 950° C. for about 2 hours, and cooled from about 950° C. to about 20° C. over about 3 hours. However, the specific manner in which the hydrogen sensing material of this disclosure is prepared is not limiting within this disclosure, provided that the hydrogen sensing material is comprised of gold nanoparticles dispersed in an inert matrix as defined herein.

At FIG. 1, the monitored stream G is some portion of a high temperature gas stream, where both the monitored stream G and the high temperature gas stream have a temperature greater than about 500° C. In an embodiment, the high temperature gas stream and the monitored stream are separated by a barrier layer, such as a dense filter layer to act as a diffusion barrier or a sieve material having an average pore size that is tailored to improve selectivity. Such an arrangement may be helpful when the high temperature gas stream is comprised of a molecular constituent outside of $H_2$ which may act to impact the plasmon resonance optical absorption peak of the hydrogen sensing material. For example, a sieve material may be utilized to exclude the molecular constituent from the monitored stream by selecting a sieve material having an average pore size less than the molecular diameter of the molecular constituent to be excluded. Exemplary sieves include aluminosilicate minerals, clays, porous glasses, microporous charcoals, zeolites, active carbons, or synthetic compounds which display a standardized average pore size, such as pore size 3A, pore size 4A, etc. In a similar manner, the dense filter layer can be selected such that the diffusion of species other than H in an ionic, atomic, or diatomic form is much more sluggish. Exemplary filters include films comprised of $SnO_2$, $SiO_2$, Palladium alloys, and others materials known for the selective filtering of hydrogen. An appropriately defined barrier layer can also protect the underlying hydrogen sensing layer from the presence of particulates and undesirable corrosive species that may have a deleterious effect on long term stability of the sensing layer. In an embodiment, a first surface of the barrier material is contacted with the high temperature gas stream, and the monitored stream is withdrawn from a second surface of the barrier material.

Figure 9:
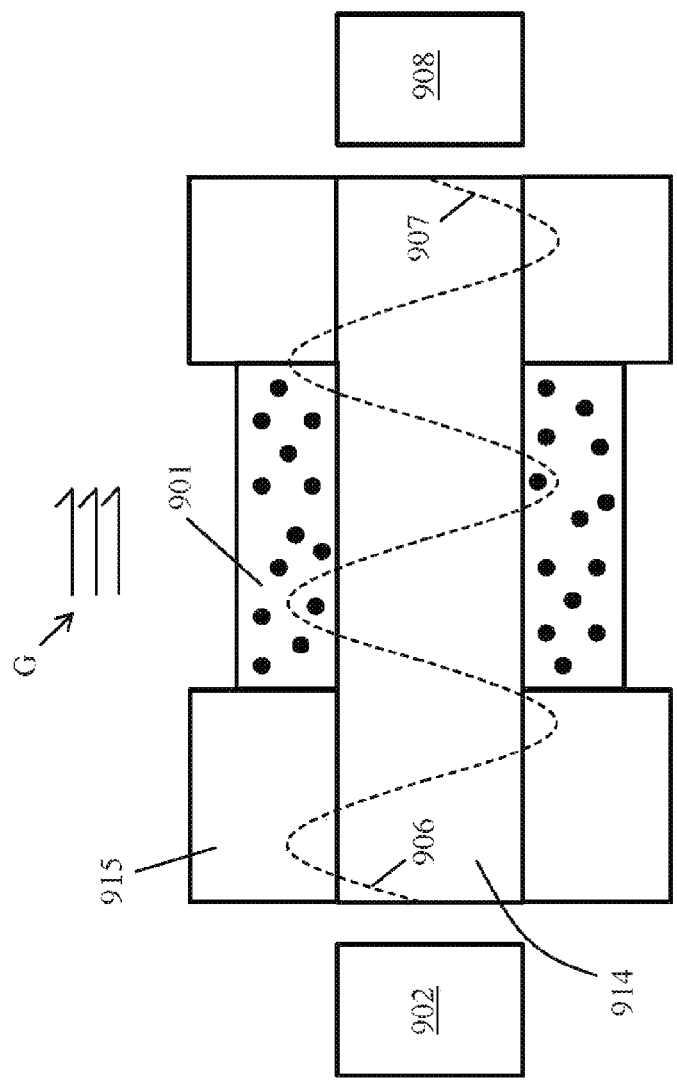
FIG. 9 illustrates a hydrogen sensing material configuration suitable for the detection of $H_2$ using a waveguide sensor.

In another embodiment, the hydrogen sensing material is illuminated by an evanescent wave created in a waveguide, such as a fiber optic cable. This particular embodiment is illustrated at FIG. 9. The waveguide is comprised of a core material 914 in contact with a cladding material 915, where core material 914 has a refractive index greater than cladding material 915. For example, core material 914 and cladding material 915 may be comprised of silica and various additions such as germanium, titanium, phosphorous, boron, fluorine, or other dopants in order to alter the respective refractive indices and meet the necessary criteria. At FIG. 9, light source 902 emits visible light into core material 914, generating evanescent wave 906 penetrating cladding material 915. As is understood, the optical power and penetration depth of the evanescent wave into cladding 915 can be described by Beer-Lambert law. See e.g., Dickinson et al., "Convergent, Self-Encoded Bead Sensor Arrays in the design of an Artificial Nose," *Anal. Chem.* 71 (1999), among others. As is similarly understood, the optical power coupled into the evanescent field may be improved by various methods such as bending, optimizing the relative refractive indices of the core and cladding, use of hollow fibers, and other methods. See e.g., Elosua et al., "Volatile Organic Compound Optical Fiber Sensors: A Review," *Sensors* 6 (2006), among others.

At FIG. 9, hydrogen sensing material 901 having the properties disclosed is placed in contact with core material 914 such that hydrogen sensing material 901 is illuminated by evanescent wave 906 as illustrated. Hydrogen sensing material 901 is additionally in contact with monitored stream G, comprised of gaseous constituents at a temperature greater than about 500° C. Exiting light 907 is collected by probe 908. Interaction of hydrogen sensing material 901 with monitored stream G and illumination by evanescent wave 906 enables the detection of $H_2$ through monitoring of the resulting plasmon resonance peak positions, as earlier described.

Thus, provided here is a method for $H_2$ sensing in a gas at temperatures greater than about 500° C. which utilizes shifts in a plasmon resonance peak position generated by a hydrogen sensing material. The hydrogen sensing material is comprised of a plurality of gold nanoparticles dispersed in a wide bandgap matrix with a low oxygen ion conductivity. The method disclosed offers significant advantage over materials typically utilized for plasmon-based high temperature sensing such as yttria-stabilized zirconia (YSZ) or $TiO_2$, including enhanced thermal stability, relative insensitivity to reducing gases beyond $H_2$, increased stability of nanoparticle diameter, tunability of effective refractive indices for compatibility with optical waveguide based sensors, among others.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of monitoring hydrogen in a high temperature gas stream comprising:
generating the high temperature gas stream, where the high temperature gas stream has a temperature greater than about 500° C.;
placing a hydrogen sensing material in the high temperature gas stream, where the hydrogen sensing material is comprised of,
an inert matrix, where the inert matrix is stable at the gas stream temperature, and where the inert matrix is optically transparent over a light wavelength range, and where the inert matrix has a bandgap greater than or equal to 5 eV and has an oxygen ion conductivity of less than $10^{-7}$ S/cm at a temperature of 700° C.,
a plurality of gold nanoparticles dispersed in the inert matrix, where an individual gold nanoparticle in the plurality of gold nanoparticles is comprised of elemental gold, and where the plurality of gold nanoparticles have an average nanoparticle diameter of less than about 100 nanometers;
contacting the hydrogen sensing material with a monitored stream, where the monitored stream is at least a portion of the high temperature gas stream, and where the monitored stream has a temperature greater than about 500° C., and illuminating the hydrogen sensing material with a light source emitting incident light;
collecting exiting light, where the exiting light is light that originates at the light source and is transmitted or reflected by the hydrogen sensing material, and monitoring a plasmon resonance peak position based on a comparison of the incident light and the exiting light using absorption spectroscopy; and
detecting hydrogen based on a peak shift of the plasmon resonance peak position, thereby monitoring hydrogen in the high temperature gas stream.

2. The method of claim 1 where the gas stream temperature is less than about 1000° C. and where the average nanoparticle diameter is less than about 50 nanometers.

3. The method of claim 2 where the plasmon resonance peak position is from about 500 nm to about 600 nm.

4. The method of claim 3 where the plurality of nanoparticles is comprised of individual nanoparticles separated by an average nanoparticle spacing, and the average nanoparticle spacing is greater than about 5 times the average nanoparticle diameter.

5. The method of claim 4 where the inert matrix is comprised of $SiO_2$, $Al_2O_3$, $Si_3N_4$, or combinations thereof.

6. The method of claim 1 where the high temperature gas stream is comprised of a molecular gas constituent, and further comprising:
utilizing a barrier layer, where the barrier layer material has a first surface and a second surface, where the first surface and the second surface are separated by at least some portion of the barrier layer; and
contacting the first surface of the barrier layer and the high temperature gas stream, and withdrawing the monitored stream from the second surface of the barrier layer.

7. The method of claim 1 where the incident light is comprised of visible light.

8. The method of claim 1 further comprising:
ascertaining a matrix refractive index, where the matrix refractive index is the refractive index of the inert matrix;
providing a waveguide comprised of a core material, where the core material has a refractive index greater than the matrix refractive index;
placing the hydrogen sensing material in contact with the core material; and
emitting the incident light from the light source into the core material and generating an evanescent wave in the hydrogen sensing material, thereby illuminating the hydrogen sensing material with the light source emitting the incident light.

9. The method of claim 8 where the waveguide is a fiber optic cable having a first end and a second end, and further comprising:
issuing the incident light from the light source into the core material at the first end of the fiber optic cable, thereby emitting the incident light from the light source into the core material and generating the evanescent wave in the hydrogen sensing material; and
gathering emitted light from the core material at the second end of the fiber optic cable, thereby collecting the exiting light.

10. The method of claim 9 where the core material is comprised of $SiO_2$, and where the inert matrix is comprised of $SiO_2$.

11. The method of claim 9 where the core material is comprised of $Al_2O_3$, and where the inert matrix is comprised of $SiO_2$ or a mixture of $SiO_2$ and $Al_2O_3$.

12. A method of monitoring hydrogen in a high temperature gas stream comprising:
generating the high temperature gas stream, where the high temperature gas stream has a temperature greater than about 500° C. and less than about 1000° C.;
placing a hydrogen sensing material in the high temperature gas stream, where the hydrogen sensing material is comprised of,
an inert matrix, where the inert matrix is stable at the gas stream temperature, and where the inert matrix is optically transparent over a light wavelength range, and where the inert matrix has a bandgap greater than or equal to 5 eV and has an oxygen ion conductivity less than approximately $10^{-7}$ S/cm at a temperature of 700° C.,
a plurality of gold nanoparticles dispersed in the inert matrix, where an individual gold nanoparticle in the plurality of gold nanoparticles is comprised of elemental gold, and where the plurality of gold nanoparticles have an average nanoparticle diameter of less than about 50 nanometers, and where the plurality of gold nanoparticles is comprised of individual gold nanoparticles separated by an average nanoparticle spacing, where the average nanoparticle spacing is greater than about 5 times the average nanoparticle diameter;
contacting the hydrogen sensing material with a monitored stream, where the monitored stream is at least a portion of the high temperature gas stream, and where the monitored stream has a temperature greater than about 500° C. and less than about 1000° C., and illuminating the hydrogen sensing material with a light source emitting incident light;

collecting exiting light, where the exiting light is light that originates at the light source and is transmitted or reflected by the hydrogen sensing material, and monitoring a plasmon resonance peak position based on a comparison of the incident light and the exiting light using absorption spectroscopy; and detecting hydrogen based on a peak shift of the plasmon resonance peak position, thereby monitoring hydrogen in the high temperature gas stream.

13. The method of claim 12 where the incident light is comprised of visible light and where the plasmon resonance peak position is within a range from about 400 nm to about 750 nm.

14. The method of claim 13 where the inert matrix is comprised of $SiO_2$, $Al_2O_3$, $Si_3N_4$, or combinations thereof.

15. The method of claim 13 further comprising:
ascertaining a matrix refractive index, where the matrix refractive index is the refractive index of the inert matrix;
providing a fiber optic cable having a first end and a second end, where the fiber optic cable is comprised of a core material, where the core material has a refractive index greater than the matrix refractive index;
emitting the incident light from the light source into the core material at the first end of the fiber optic cable and generating an evanescent wave in the cladding material of the waveguide;
placing the hydrogen sensing material in contact with the core material at a location between the first end of the fiber optic cable and the second end of the fiber optic cable, and emitting the incident light from the light source into the core material at the first end of the fiber optic cable, thereby generating an evanescent wave in the hydrogen sensing material, and thereby illuminating the hydrogen sensing material with the light source emitting the incident light; and
gathering emitted light from the core material at the second end of the fiber optic cable, thereby collecting the exiting light.

16. The method of claim 15 where the core material is comprised of $SiO_2$ and where the inert matrix is comprised of a doped $SiO_2$, where the doped $SiO_2$ is comprised of $SiO_2$ and a dopant, and where a refractive index of the doped $SiO_2$ is less than a refractive index of the core material.

17. The method of claim 16 where the dopant is $MgF_2$.

18. The method of claim 15 where the high temperature gas stream is comprised of a molecular gas constituent, and further comprising:
utilizing a barrier layer, where the barrier layer material has a first surface and a second surface, where the first surface and the second surface are separated by at least some portion of the barrier layer; and
contacting the first surface of the barrier layer and the high temperature gas stream, and withdrawing the monitored stream from the second surface of the barrier layer.

19. A method of monitoring hydrogen in a high temperature gas stream comprising:
generating the high temperature gas stream, where the high temperature gas stream has a temperature greater than about 500° C. and less than about 1000° C.;
placing a hydrogen sensing material in the high temperature gas stream, where the hydrogen sensing material is comprised of,
an inert matrix, where the inert matrix is stable at the gas stream temperature, and where the inert matrix is optically transparent over a light wavelength range, and where the inert matrix has a bandgap greater than or equal to 5 eV and has an oxygen ion conductivity less than $10^{-7}$ S/cm at a temperature of 700° C.,
a plurality of gold nanoparticles dispersed in the inert matrix, where an individual gold nanoparticle in the plurality of gold nanoparticles is comprised of elemental gold, and where the plurality of gold nanoparticles have an average nanoparticle diameter of less than about 50 nanometers, and where the plurality of gold nanoparticles is comprised of individual gold nanoparticles separated by an average nanoparticle spacing, where the average nanoparticle spacing is greater than about 5 times the average nanoparticle diameter;
ascertaining a matrix refractive index, where the matrix refractive index is the refractive index of the inert matrix;
providing a fiber optic cable having a first end and a second end, where the fiber optic cable is comprised of a core material, where the core material has a refractive index greater than the matrix refractive index, and placing the hydrogen sensing material in contact with the core material at a location between the first end of the fiber optic cable and the second end of the fiber optic cable;
contacting the hydrogen sensing material with a monitored stream, where the monitored stream is at least a portion of the high temperature gas stream, and where the monitored stream has a temperature greater than about 500° C. and less than about 1000° C.,
emitting incident light from a light source into the core material at the first end of the fiber optic cable and generating an evanescent wave in the hydrogen sensing material;
gathering exiting light from the core material at the second end of the fiber optic cable, and monitoring a plasmon resonance peak position based on a comparison of the incident light and the exiting light using absorption spectroscopy; and
detecting hydrogen based on a peak shift of the plasmon resonance peak position, thereby monitoring hydrogen in the high temperature gas stream.

20. The method of claim 19 where the inert matrix is comprised of $SiO_2$, $Al_2O_3$, $Si_3N_4$, or combinations thereof.

* * * * *